US006388138B1

(12) United States Patent
Lee

(10) Patent No.: US 6,388,138 B1
(45) Date of Patent: May 14, 2002

(54) PROCESS FOR PRODUCING A MAGNESIUM DI[TETRAKIS(FARYL)BORATE] AND PRODUCTS THEREFROM

(75) Inventor: John Y. Lee, Baton Rouge, LA (US)

(73) Assignee: Albemarle Corporation, Richmond, VA (US)

(*) Notice: Subject to any disclaimer, the term of this patent is extended or adjusted under 35 U.S.C. 154(b) by 40 days.

(21) Appl. No.: 09/724,647

(22) Filed: Nov. 28, 2000

Related U.S. Application Data

(62) Division of application No. 09/453,606, filed on Dec. 3, 1999, now Pat. No. 6,169,208.

(51) Int. Cl.$^7$ .............................................. C07F 5/02

(52) U.S. Cl. ............................................. 568/6; 564/8

(58) Field of Search ..................... 568/1, 6, 8

(56) References Cited

U.S. PATENT DOCUMENTS

| | | | |
|---|---|---|---|
| 4,808,282 A | 2/1989 | Gregory | 204/58.5 |
| 5,070,161 A | 12/1991 | Nakano et al. | 526/193 |
| 5,078,974 A | 1/1992 | Ashby et al. | 422/187 |
| 5,096,936 A | 3/1992 | Seko et al. | 522/31 |
| 5,189,222 A | 2/1993 | Ashby et al. | 568/1 |
| 5,223,591 A | 6/1993 | Nyander et al. | 526/204 |
| 5,340,898 A | 8/1994 | Cavezzan et al. | 528/19 |
| 5,399,781 A | 3/1995 | Doellein | 568/6 |
| 5,420,355 A | 5/1995 | Ikeda et al. | 568/6 |
| 5,468,902 A | 11/1995 | Castellanos et al. | 568/6 |
| 5,473,036 A | 12/1995 | Piotrowski et al. | 528/4 |
| 5,488,169 A | 1/1996 | Ikeda et al. | 568/3 |
| 5,493,056 A | 2/1996 | Ikeda et al. | 568/6 |
| 5,510,536 A | 4/1996 | Ikeda et al. | 568/6 |
| 5,514,728 A | 5/1996 | Lamanna et al. | 522/31 |
| 5,600,003 A | 2/1997 | Baur et al. | 568/1 |
| 5,670,682 A | 9/1997 | Sangokoya | 556/181 |
| 5,693,867 A | 12/1997 | Bauer et al. | 568/1 |
| 5,919,983 A | 7/1999 | Rosen et al. | 568/3 |
| 6,129,863 A | 10/2000 | Lee et al. | 260/665 G |

FOREIGN PATENT DOCUMENTS

| | | |
|---|---|---|
| EP | 0331496 | 9/1989 |
| EP | 0913400 | 5/1999 |
| JP | 9295984 | 11/1997 |
| JP | 9295985 | 11/1997 |
| JP | 10316686 | 12/1998 |
| WO | 9807798 | 2/1998 |
| WO | 9822470 | 5/1998 |

OTHER PUBLICATIONS

Bond, et al., "Liquid Clathrates", J. Chem. Soc., Commun., 1989, pp. 1910–1911.
Bahr et al., "Trityl Tetrakis(3,5–bis(trifluoromethyl)phenyl)–borate: A New Hydride Abstraction Reagent", J. Org. Chem., 1992, vol. 57, No. 20, pp. 5545–5547.
Brookhart et al., "[(3,5–(CF$_3$)$_2$C$_6$H$_3$)$_4$B]–[H(OEt$_2$)$_2$]: A Convient Reagent for Generation and Stabilization of Cationic, Highly Electrophillic Organometallic Complexes", Organometallics, vol. 11, 1992, pp. 3920–3922.
Chien et al., "Isospecific Polymerization of Propylene Catalyzed by rac–Ethylenebis(indenyl)methylzirconium "Cation"", Journal Am. Chem. Soc. 1991, vol. 113, p. 8570–8571.
Fujiki et al., "Synthesis and Lipophilicities of Tetraarylborate ions substituted with many Trifluoromethyl Groups", Journal of Fluorine Chemistry, vol. 57, 1992, pp. 307–321.
Gol'dberg et al., "Synthesis of Sodium Tetrakis[3,5–DI(Trifluoromethyl)Phenyl]Borate", Zhurnal organicheskoi Khimi, 1989, vol. 25, No. 5, pp. 1099–1102 (translation thereof), pp. 989–991.
Golden et al., "Lithium–Mediated Organofluorine Hydrogen Bonding: Structure of Lithium Tetreakis(3,5–bis(trifluoromethyl)phenyl)borate Tetrahydrate", Inorg. Chem. vol. 33, 1994, pp. 5374–5375.
Hayashi et al., "A Novel Chiral Super–Lewis Acidic Catalyst for Enantioselective Synthesis", J. Am. Chem. Soc., 1996, vol. 118, No. 23, pp. 5502–5503.
Hughes et al., "Synthesis and Structure of the Thallium(I) Salt of the Tetrakis [3,5–bis(trifluoromethyl)phenyl]borate Anion", Inorg. Chem. vol. 36, 1997, pp. 1726–1727.
Jia et al., "Cationic Metallocene Polymerization Catalysts Based on Tetrakis(pentafluorophenyl)borate and Its Derivatives. Probing the Limits of Anion "Noncoordination" via a Synthetic, Solution Dynamic, Structural, and Catalytic Olefin Polymerization Study", Organometallics, 1997, vol. 16, p. 842–857.

(List continued on next page.)

Primary Examiner—Jean F. Vollano
(74) Attorney, Agent, or Firm—Philip M. Pippenger

(57) ABSTRACT

A solution comprising a halomagnesium tetrakis($^F$aryl)borate in a liquid organic medium, wherein the liquid organic medium is comprised of one or more liquid dihydrocarbyl ethers, one or more liquid hydrocarbons, one or more liquid halogenated hydrocarbons, or mixtures thereof, is contacted with water. This produces magnesium di[tetrakis($^F$aryl)borate] in the organic phase of a two-phase water/liquid organic medium. The magnesium di[tetrakis ($^F$aryl)borate] can be, but need not be, isolated. A protic ammonium salt, an onium salt, or a triarylmethyl salt can be reacted with the magnesium di[tetrakis($^F$aryl)borate] to produce the corresponding protic ammonium, onium, or triarylmethyl tetrakis($^F$aryl)borate. The magnesium di[tetrakis ($^F$aryl)borate] can instead be reacted with a metal salt to form a metal tetrakis($^F$aryl)borate. The produced metal tetrakis($^F$aryl)borate can be further reacted with a protic ammonium salt, an onium salt, or a triarylmethyl salt to yield a protic ammonium, onium, or triarylmethyl tetrakis($^F$aryl) borate. Certain of these tetrakis($^F$aryl)borates can be conveniently purified via the formation of a liquid clathrate at ambient temperatures.

15 Claims, No Drawings

OTHER PUBLICATIONS

Jia et al., "Protected (Fluoroaryl)borates as Effective Counteranions for Cationic Metallocene Polymerization Catalysts", Organometallics, vol. 14, 1995 pp. 3135–3137.

Chem. Abstract #17030, Line H, Myl, et al., "Preparation of Sodium Tetraphenylborate", Benzene Derivatives, 1959, 1 page.

Nesmeyanov et al., "Synthesis of Sodium Tetraphenylboron", Izv. Akad. Nauk SSSR, Otd. Khim. Nauk, 1955, pp. 187. (Translation pp. 167).

Nishida et al., "Tetrakis[3,5–bis(trifluoromethyl]borate. Highly Lipophilic Stable Anionic Agent for Solvent–extraction of Cations", Bull Chem. Soc. Jpn., vol. 57, No. 9, 1984, pp. 2600–2604.

Vandeberg et al., "Studies in the Tetraarylborates Part III. The Preparation and Reagent Properties of Sodium Tetrakis(p–Trifluoromethylphenyl)Borate and Sodium Tetrakis(m–Fluorophenyl)Borate", Analytica Chimica Acta, Elsevier Publishing Company, Amsterdam, 1969, vol. 44, pp. 175–183.

Chemical Abstract, #15921, line G, Vit, Jaroslav, "Preparaing Sodium Tetraarylborates, esp. Sodium Tetraphenylborate", Organometallic Compounds, vol. 64, 1966, col. 15921, 1 page.

Chemical Abstract, #124402W, Wakabayashi et al., "Agrochemical and Industrial Microbicides Containing Tetraphenylborates", 1988, vol. 109, p. 254.

Chemical Abstract, #6607, Line D, Wittig et al., "Complex Formation with Triphenylboron. III.", 1951, vol. 46, 1 page.

Chemical Abstract, #85:86471u, Khol'kin et al., "Synthesis of Metal Tetraphenylborates by the Exchange Extraction Method", Izv. Sib. Otd. Akad. Nauk., 1976, p. 595.

Chemical Abstract, #125: 196680p. of FR 2,727,416, 1996, p. 20.

Chemical Abstract, #129: 317638z, of WO 98 46,647, 1998, p. 831.

Atwood, Jerry L., Coordination Chemistry of Aluminum, Chapter 6, "Anionic and Cationic Organoaluminum Compounds", 1993, p. 197–232.

Chemical Abstract, #214696R, Wakabayashi et al., "Pyridinium and Quinolinium Tetraphenylborate Salts as Agrochemical and Industrial Microbicides", Organometallics, 1989, vol. 111, p. 611.

Wittig et al., "Uber Komplexbildung mit Triphenyl–bor (III. Mitt.)", Annalen der Chemie, 1951, vol. 573, pp. 195–209.

Coleman et al., "Air–Stable Liquid Clathrates. 1. Crystal Structure of [NBu$_4$][Br$_3$] and Reactivity of the [NBu$_4$][Br$_3$] 5 C$_6$H$_6$ Liquid Clathrate", Journal of Crystallographic and Spectroscopic Research, vol. 20, No. 2, 1990, pp. 199–201.

Chem. Abstract, vol. 110, 1989, of JP 63,108,074, 1988, p. 720.

"Periodic Table of the Elements", Chem. And Eng. News, 1985, pp. 26–27.

US 6,388,138 B1

PROCESS FOR PRODUCING A MAGNESIUM DI[TETRAKIS($^F$ARYL)BORATE] AND PRODUCTS THEREFROM

REFERENCE TO RELATED APPLICATION

This is a division of prior commonly-owned application Ser. No. 09/453,606, filed Dec. 3, 1999 now U.S. Pat. No. 6,169,208.

TECHNICAL FIELD

This invention relates to a method for making a magnesium di[tetrakis($^F$aryl)borate], which can be further reacted with an organic cation salt to produce the corresponding organic cation tetrakis($^F$aryl)borate. When the organic cation is a protic ammonium cation or a triarylmethyl cation, the tetrakis($^F$aryl)borate salt is useful as a cocatalyst for metallocene-catalyzed polymerization. When the organic cation is an onium cation, the tetrakis($^F$aryl)borate salt is useful as an initiator in the crosslinking of polyorganosiloxanes.

BACKGROUND

It is known that when a halomagnesium salt of a tetrakis (aryl)borate anion is obtained, other magnesium salts are usually also present. Often, the removal of these other magnesium salts is necessary because they interfere with the intended use of the halomagnesium salt of the tetrakis(aryl) borate anion. Reaction of the halomagnesium tetrakis(aryl) borate with an alkali metal salt to form an alkali metal tetrakis(aryl)borate is a separation method that has been used. For various descriptions of this method, see Nishida et al., *Bull. Chem. Soc. Jpn.*, 1984, 57, 2600; Goldberg et al., *Zhurnal Organicheskoi Khimii*, 1989, 25, 1099; Fujiki et al., *J. Fluorine Chemistry*, 1992, 57, 307; and EP 913,400. A method which cleanly separates other magnesium salts from the halomagnesium salt of the tetrakis(aryl)borate without the introduction of a reagent such an alkali metal salt would be desirable.

Once a suitably pure tetrakis(aryl)borate salt is obtained, it can be reacted with an appropriate compound to yield an organic cation salt of the tetrakis(aryl)borate. It is often desirable to purify these organic cation tetrakis(aryl)borates. It is known that phenyl(dimethyl)ammonium tetrakis (pentafluorophenyl)borate can be purified via the formation of a liquid clathrate. The liquid clathrate is formed in toluene at temperatures typically above 55° C.; at temperatures less than about 55° C., the compound precipitates. While the liquid clathrate provides relatively pure phenyl(dimethyl) ammonium-tetrakis(pentafluorophenyl)borate, it is inconvenient to keep the clathrate-containing solution and apparatus at elevated temperatures while performing necessary manipulations. A more convenient purification method is desirable.

SUMMARY OF THE INVENTION

This invention provides for the formation of a magnesium di[tetrakis($^F$aryl)borate], which can be, but need not be, isolated. The magnesium di[tetrakis($^F$aryl)borate] can be reacted, in isolated or unisolated form, with a salt of a desired cation to form the desired cation tetrakis($^F$aryl) borate. Certain of these tetrakis($^F$aryl)borates can be conveniently purified via the formation of a liquid clathrate at ambient temperatures.

A first embodiment of this invention is a process which comprises contacting i) a solution comprising a liquid organic medium, which is substantially immiscible with water, and a halomagnesium tetrakis($^F$aryl)borate, and ii) water, in such proportions that a two-phase mixture is obtained. A solution of a magnesium di[tetrakis($^F$aryl) borate] in the organic phase of a two-phase water/liquid organic medium is produced. Each aryl group of the tetrakis ($^F$aryl)borate has bonded directly to an aromatic ring at least two fluorine atoms, or at least two perfluorohydrocarbyl groups, or at least one fluorine atom and at least one perfluorohydrocarbyl group. The liquid organic medium is comprised of one or more liquid dihydrocarbyl ethers, one or more liquid hydrocarbons, one or more liquid halogenated hydrocarbons, or mixtures thereof.

The borate anion has four fluorine-containing aryl groups, each of which has bonded directly to an aromatic ring at least two fluorine atoms, or at least two perfluorohydrocarbyl groups, or at least one fluorine atom and at least one perfluorohydrocarbyl group. It is preferred that at least two fluorine atoms, or at least two perfluorohydrocarbyl groups are bonded directly to an aromatic ring. Each position on the aromatic ring(s) of the $^F$aryl group that is not a fluorine atom or a perfluorohydrocarbyl group is substituted by a hydrogen atom, a hydrocarbyl group, an alkoxy group, or a silyl group. The $^F$aryl groups may be the same or different from each other; it is preferred that all four $^F$aryl groups are the same.

Another embodiment of this invention is a process which comprises mixing at least a portion of the magnesium di[tetrakis($^F$aryl)borate] produced in the first embodiment in a liquid medium with a salt selected from a) a protic ammonium salt, b) an onium salt, and c) a triarylmethyl salt, wherein the triarylmethyl cation has three aryl groups bound to a central carbon atom, to produce a protic ammonium tetrakis($^F$aryl)borate, an onium tetrakis($^F$aryl)borate, or a triarylmethyl tetrakis($^F$aryl)borate. The protic ammonium cation has the formula [R$_3$NH]$^\oplus$, in which each R is independently a hydrocarbyl group containing up to about thirty carbon atoms, and the onium cation has the formula [ER$_n$]$^\oplus$, wherein E is an element of any of Groups 15–17 of the Periodic Table, wherein each R is independently a hydrocarbyl group containing up to about thirty carbon atoms, and wherein n is equal to the valence of E plus one. For labeling of the groups of the Periodic Table, see for example, the Periodic Table appearing in *Chemical & Engineering News*, 1985, 69, 26.

Still another embodiment of this invention is a process which comprises mixing, in a liquid medium, at least a portion of the magnesium di[tetrakis($^F$aryl)borate] produced in the first embodiment and at least one metal salt. An inorganic metal tetrakis($^F$aryl)borate is produced.

Yet another embodiment of this invention is a process which comprises mixing, in a liquid medium, at least a portion of the metal tetrakis($^F$aryl)borate produced in the preceding embodiment with a salt selected from a) a protic ammonium salt, b) an onium salt, and c) a triarylmethyl salt, to produce a protic ammonium tetrakis($^F$aryl)borate, an onium tetrakis($^F$aryl)borate, or a triarylmethyl tetrakis ($^F$aryl)borate. The protic ammonium cations, onium cations, and triarylmethyl cations are as described above.

Further embodiments of this invention will be apparent from the ensuing description and appended claims.

FURTHER DETAILED DESCRIPTION OF THE INVENTION

The liquid organic medium of the solution that also comprises a halomagnesium tetrakis($^F$aryl)borate is comprised of one or more liquid dihydrocarbyl ethers, one or more liquid hydrocarbons, one or more halogenated hydrocarbons, or mixtures thereof. Those ethers, hydrocarbons, and halogenated hydrocarbons that are substantially immiscible with water, such that a two-phase mixture will be formed, are preferred. Ethers that may be used include, for example, diethyl ether, di-n-propyl ether, diisopropyl ether, tert-butyl ethyl ether, diheptyl ether, and similar compounds. Preferred ethers are diethyl ether and diisopropyl ether, especially diethyl ether. Suitable hydrocarbons include pentane, hexane, methylcyclohexane, heptane, octane, cyclooctane, nonane, benzene, toluene, and xylenes. Halogenated hydrocarbons that may be used include dichloromethane, trichloromethane, 1,2-dichloroethane, 1-bromo-2-chloroethane, 1-bromopropane, (chloromethyl)cyclopropane, 1-bromobutane, 1-bromo-2-ethylbutane, 1,1-dichloro-3,3-dimethylbutane, cyclobutyl chloride, neopentyl chloride, 1-bromo-5-chloropentane, cyclopentyl bromide, 1,6-dibromohexane, trans-1,2-dichlorocyclohexane, 1-chloroheptane, and 1,8-dichlorooctane.

The proportions of water and liquid organic medium are such that either component can be present in a larger amount than the other; however, a large excess of either is unnecessary. Preferred ratios of water to liquid organic medium are in the range of from about 0.2 parts to about three parts by volume of water per part by volume of liquid organic medium.

The halogen atom of the halomagnesium moiety of the halomagnesium tetrakis($^F$aryl)borate may be a chlorine atom, bromine atom, or iodine atom. Preferred halogen atoms are chlorine and bromine; most preferred is a bromine atom. Thus, the most preferred halomagnesium moiety is a bromomagnesium moiety.

Throughout this document, the term "$^F$aryl group" shall be understood to mean, as described above, a fluorine-containing aryl group, which has bonded directly to an aromatic ring at least two fluorine atoms, or at least two perfluorohydrocarbyl groups, or at least one fluorine atom and at least one perfluorohydrocarbyl group. It is preferred that at least two fluorine atoms or at least two perfluorohydrocarbyl groups are bonded directly to an aromatic ring. Each position on the aromatic ring(s) of the $^F$aryl group that is not a fluorine atom or a perfluorohydrocarbyl group is substituted by a hydrogen atom, a hydrocarbyl group, an alkoxy group, or a silyl group. The aromatic ring of the $^F$aryl group may be, but is not limited to, benzene, naphthalene, anthracene, biphenyl, phenanthrene, or indene. Benzene is the preferred aromatic moiety. The perfluorohydrocarbyl groups include alkyl and aryl perfluorocarbons; suitable perfluorohydrocarbyl groups are, for example, trifluoromethyl, pentafluoroethyl, pentafluorophenyl, and heptafluoronaphthyl. The hydrocarbyl groups of the aryl groups are preferably $C_1$ to $C_{18}$ alkyl groups or $C_6$ to $C_{20}$ aryl or aralkyl groups. Examples of suitable hydrocarbyl groups are methyl, ethyl, isopropyl, tert-butyl, cyclopentyl, methylcyclohexyl, decyl, phenyl, tolyl, xylyl, benzyl, naphthyl, and tetrahydronaphthyl. The alkoxy groups preferably have $C_1$ to $C_6$ alkyl moieties. Some examples of alkoxy groups are methoxy, ethoxy, isopropoxy, methylcyclopentoxy, and cyclohexoxy. The silyl groups preferably have $C_1$ to $C_{18}$ alkyl groups or $C_6$ to $C_{20}$ aryl or aralkyl groups. Suitable silyl groups include trimethylsilyl, triisopropylsilyl, tert-butyl(dimethyl)silyl, tridecylsilyl, and triphenylsilyl. Examples of $^F$aryl groups that may be present on the borate moiety in this invention include 3,5-bis(trifluoromethyl)phenyl, 2,4,6-tris(trifluoromethyl)-phenyl, 4-[tri(isopropyl)silyl]-tetrafluorophenyl, 4-[dimethyl(tert-butyl)silyl]-tetrafluorophenyl, 4'-(methoxy)-octafluorobiphenylyl, 2,3-bis(pentafluoro-ethyl)naphthyl, 2-(isopropoxy)-hexafluoronaphthyl, 9,10-bis(heptafluoropropyl)-hepta-fluoroanthryl, 9,10-bis(p-tolyl)-heptafluorophenanthryl, and 1-(trifluoromethyl)-tetrafluoroindenyl. It is preferred that at most two substituents on the ring of the aryl group are hydrocarbyl, perfluorohydrocarbyl, or alkoxy, while the rest of the substituents are fluorine atoms.

It is highly preferred to have $^F$aryl groups in which the all of the substituents are fluorine atoms. Examples of such groups are pentafluorophenyl, 4-nonafluorobiphenylyl, 2-nonafluorobiphenylyl, 1-heptafluoronaphthyl, 2-heptafluoronaphthyl, 7-nonafluoroanthryl, 9-nonafluorophenanthryl, and analogous groups. The most highly preferred perfluoroaryl group is pentafluorophenyl; thus, the most highly preferred borate is tetrakis(pentafluorophenyl)borate.

A magnesium di[tetrakis($^F$aryl)borate] is produced by contacting water and the solution comprising a liquid organic medium and a halomagnesium tetrakis($^F$aryl)borate. These components are usually at room temperature when mixed together. In the resultant two-phase mixture, the magnesium di[tetrakis($^F$aryl)borate] is in the organic phase, which can easily be separated from the aqueous phase. Removal of the liquid organic medium from the separated organic phase yields solid magnesium di[tetrakis($^F$aryl)borate]. Magnesium salts produced in the formation of the magnesium di[tetrakis($^F$aryl)borate] migrate to the aqueous layer. When other magnesium salts are present in the liquid organic medium, they are also expected to be in the water layer of the resultant two-phase mixture.

During the course of the reaction, some heat may be produced, raising the temperature of the reaction mixture. The mixture may be heated, provided that the temperature does not exceed the thermal decomposition temperature of the magnesium di[tetrakis($^F$aryl)borate]. A preferred contact time for the components of the reaction is in the range of from about ten minutes to about eight hours. More preferably, the contact time is from about fifteen minutes to about six hours.

For the contacting of a magnesium di[tetrakis($^F$aryl) borate] and a triarylmethyl salt, the liquid medium is comprised of one or more liquid hydrocarbons, halogenated hydrocarbons, ethers, or mixtures thereof. Suitable hydrocarbons include linear, branched, and cyclic saturated hydrocarbons, and aromatic hydrocarbons. Examples of suitable hydrocarbons include pentane, hexane, cyclohexane, methylcyclohexane, heptane, cyclooctane, nonane, benzene, toluene, xylene, and the like. Halogenated hydrocarbons that are suitable include dichloromethane, trichloromethane, 1,2-dichloroethane, 1-bromo-2-chloroethane, 1-bromopropane, (chloromethyl) cyclopropane, 1-bromobutane, 1-bromo-2-ethylbutane, 1,1-dichloro-3,3-dimethylbutane, cyclobutyl chloride, neopentyl chloride, 1-bromo-5- chloropentane, cyclopentyl bromide, 1-fluorohexane, 1,6-dibromohexane, trans-1,2-dichlorocyclohexane, 1-chloroheptane, and 1,8-dichlorooctane. Examples of ethers that may be used include diethyl ether, ethyl n-propyl ether, di-n-propyl ether, diisopropyl ether, di-n-butyl ether, tetrahydrofuran, methyltetrahydrofuran, 1,4-dioxane, 1,3-dioxolane, cyclohexylmethyl ether, glyme (the dimethyl ether of ethylene glycol), diglyme (the dimethyl ether of diethylene glycol), triglyme, and tetraglyme. Preferred as the liquid organic solvent are saturated hydrocarbons, particularly those containing up to about ten carbon atoms. Also preferred are liquid aromatic hydrocarbons; particularly preferred is toluene. Preferably, the liquid organic solvent is dry, and it is preferred that the reaction is conducted in an inert atmosphere comprised of one or more inert gases, such as, for example, nitrogen, helium, or argon.

The term "triarylmethyl cation" refers to carbocations which have three aryl groups bound to a central carbon atom. The aryl groups of the triarylmethyl cation have from six to about twenty carbon atoms, can be the same or different, and can be substituted or unsubstituted. Examples of suitable aryl groups include phenyl, tolyl, xylyl, naphthyl, and 2-ethylnaphthyl; preferred are tolyl and phenyl; most preferred is phenyl. The most preferred triarylmethyl cation is a triphenylmethyl cation.

Many inorganic anions can be appropriate counterions for a triarylmethyl cation; examples of suitable inorganic anions include chloride, bromide, iodide, tetrafluoroborate, hexafluorophosphate, and the like. Preferred inorganic anions are the halides, especially chloride; thus, the preferred salt is triphenylmethyl chloride.

The magnesium di[tetrakis($^F$aryl)borate] can be combined with the triarylmethyl salt and the liquid medium in any order. Mixing of magnesium di[tetrakis($^F$aryl)borate] with the triarylmethyl salt prior to the addition of the liquid medium may cause the formation of a cake. Thus, it is preferred that both the liquid medium and the triarylmethyl salt are present in the reaction vessel before the magnesium di[tetrakis($^F$aryl)borate] is added.

Protic ammonium salts of the tetrakis($^F$aryl)borate can be formed from the magnesium di[tetrakis($^F$aryl)borate]. These ammonium cations have the general formula $[R_3NH]^\oplus$, wherein each R is independently a hydrocarbyl group containing up to about thirty carbon atoms. R is preferably an aliphatic or aromatic hydrocarbyl group; preferred hydrocarbyl groups include methyl and phenyl. Examples of suitable protic ammonium cations include, but are not limited to, trimethylammonium, triethylammonium, cyclohexyl(dimethyl)ammonium, tri(n-octyl)ammonium, phenyl(dimethyl)ammonium, diphenyl(ethyl)ammonium, and triphenylammonium cations. As described above for the triarylmethyl salt, many inorganic anions can be appropriate counterions for the protic ammonium cation. Again, the halides, especially chloride, are preferred inorganic anions; thus, the preferred salt is generally a protic ammonium chloride.

The protic ammonium salt can be formed shortly before reacting it with the magnesium di[tetrakis($^F$aryl)borate]; this is accomplished by reacting $R_3N$, wherein R is defined as for the protic ammonium cations, with a protic acid to form the protic ammonium cation. Preferred protic acids include hydrochloric acid, hydrobromic acid, hydroiodic acid, fluoboric acid, and hexafluorophosphoric acid; hydrochloric acid is a particularly preferred protic acid. Preferably, the protic ammonium cation is formed in aqueous solution.

The liquid medium for contacting the protic ammonium salt and magnesium di[tetrakis($^F$aryl)borate] can be any of a large variety of solvents, so long as they do not interfere with or decompose the desired reaction products. The exclusion of water is not necessary. When water is at least a part of the liquid mixture, the aqueous portion is preferably provided by the freshly-made protic ammonium salt solution. When ether is at least a part of the liquid medium, it may be provided by the alkali metal tetrakis($^F$aryl)borate solution. In such a case, though it is not considered practical to do so, the alkali metal tetrakis($^F$aryl)borate may be isolated from the ethereal phase in which it was made and dissolved in fresh ether.

Other salts, generally referred to as onium salts, can be reacted with the magnesium di[tetrakis($^F$aryl)borate] to yield the corresponding onium tetrakis($^F$aryl)borate. Onium cations are defined by the formula $[ER_n]^\oplus$, wherein E is an element of any of Groups 15–17 of the Periodic Table, each R is independently a hydrocarbyl group containing up to about thirty carbon atoms, and n is equal to the valence of E plus one. R is preferably an aliphatic or aromatic hydrocarbyl group. As an example of n, when E is sulfur, which has a valence of two, n is three. As described previously for both the triarylmethyl salts and the protic ammonium salts, many inorganic anions may be appropriate counterions for the onium cation. Preferred inorganic anions are the halides, especially chloride; thus, the preferred salt is generally an onium chloride. To form the onium tetrakis($^F$aryl)borates, standard cation exchange methods can be used. Choice(s) of solvent and temperature will vary with the particular system of onium salt and tetrakis($^F$aryl)borate chosen. Examples of suitable onium salts include, but are not limited to, diphenyliodonium chloride, tris(p-tolyl)sulfonium bromide, and tetraethylphosphonium chloride.

Generally, the magnesium di[tetrakis($^F$aryl)borate] and the triarylmethyl salt, protic ammonium salt, or onium salt are mixed together at room temperature. Mixing at room temperature is preferred because the yield of triarylmethyl, protic ammonium, or onium tetrakis($^F$aryl)borate is often much higher than when the mixture is heated. Some heat may be produced during the course of the reaction, raising the temperature of the mixture. The mixture may be heated, provided that the temperature does not exceed the thermal decomposition temperature of the product of the reaction. Heating during contacting of magnesium di[tetrakis($^F$aryl)borate] and the triarylmethyl, protic ammonium, or onium salt is preferred when a faster reaction rate is desired. Agitation of the reaction mixture is usually necessary for the reaction to proceed.

The contact time for magnesium di[tetrakis($^F$aryl)borate] and the protic ammonium salt or onium salt is preferably from about fifteen minutes to about eight hours; more preferred is a time in the range of from about forty-five minutes to about six hours. For mixing the magnesium di[tetrakis($^F$aryl)borate] and the triarylmethyl salt, the contact time at room temperature is preferably in the range of from about two hours to about thirty hours, and more preferably is in the range of from about ten hours to about twenty-four hours. A contact time for magnesium di[tetrakis($^F$aryl)borate] and the triarylmethyl salt when heating in the range of from about thirty minutes to about twenty hours is preferred; a more preferable range is from about one hour to about fifteen hours; highly preferred is a contact time in the range of from about two hours to about twelve hours.

From the magnesium di[tetrakis($^F$aryl)borate], a large variety of metal salts of the tetrakis($^F$aryl)borate anion may be produced from metal salts. The metal cation of the metal salt may be an alkali metal cation, an alkaline earth cation other than magnesium, or a transition metal cation. Examples of transition metal cations include silver, copper, gold, zinc, iron, palladium, nickel, and cobalt. Monovalent cations, such as alkali metal cations, silver(I), and copper(I), are preferred. Alkali metal cations are especially preferred because these salts can easily be dried, a useful feature when subsequent reactions and uses of the metal tetrakis($^F$aryl)borate require a dry salt. The most preferred alkali metal cations are sodium and potassium.

Suitable anions for the metal salts are almost limitless. Examples of such anions include, but are not limited to, bicarbonate, carbonate, nitrite, nitrate, phosphate, sulfite, sulfate, carboxylic acid anions (e.g., acetate, citrate, formate, oxalate, propionate, tartrate, etc.), fluoride, chloride, bromide, iodide, tetrafluoroborate, and hexafluorophosphate. Preferred anions are sulfate, bicarbonate, and carbonate; carbonate is particularly preferred. The most preferred metal salts are thus sodium carbonate and potassium carbonate. The metal salt may be combined with the magnesium di[tetrakis($^F$aryl)borate] in solid form or as a solution; a solution of the metal salt, particularly an aqueous solution, is preferred.

The amount of metal salt needed for reaction with the magnesium di[tetrakis($^F$aryl)borate] can vary with the oxidation state of the metal cation. The use of less than about one mole of positive charge per about one mole of tetrakis ($^F$aryl)borate anion may result in incomplete exchange of the magnesium for the desired metal cation. Complete exchange is generally preferred, so at least about one mole of positive charge per about one mole of tetrakis($^F$aryl) borate is preferable. More preferred is the use of slightly more than about one mole of positive charge per about one mole of tetrakis($^F$aryl)borate anion. Thus, it is preferable to use at least about two moles of positive charge per mole of magnesium di[tetrakis($^F$aryl)borate]. For example, the use of at least about one mole of potassium carbonate per mole of magnesium di[tetrakis($^F$aryl)borate] is preferred, while at least about two moles of silver nitrate per mole of magnesium di[tetrakis($^F$aryl)borate] are preferable.

For syntheses of protic ammonium, onium, and triarylmethyl salts of tetrakis($^F$aryl)borate from metal tetrakis($^F$aryl) borate salts, the reaction considerations and conditions are much the same as described above for the reactions of magnesium di[tetrakis($^F$aryl)borate] to form protic ammonium, onium, and triarylmethyl salts.

Tetrakis($^F$aryl)borate salts, including protic ammonium salts in which the protic ammonium cation is without aryl groups, onium salts, and triarylmethyl salts can form liquid clathrates in combination with at least one liquid aromatic hydrocarbon. Suitable liquid aromatic hydrocarbons include, for example, benzene, toluene, xylenes, mesitylene, cumene, cymene, and indene. Toluene is the most preferred liquid aromatic hydrocarbon. A weight ratio of tetrakis ($^F$aryl)borate salt to aromatic hydrocarbon in the range of from about 1:1.0 to about 1:3.0 is usually effective to form a stable clathrate, although it is recognized that this ratio may vary somewhat with the specific cation, tetrakis($^F$aryl) borate anion, aromatic hydrocarbon and temperature chosen. Excess aromatic hydrocarbon does not adversely affect the formation of the liquid clathrate, and a quantity in excess of the amount that is necessary to form the liquid clathrate is preferably used. The addition of heat is sometimes necessary to induce clathrate formation; in such cases, it is preferred to heat to a temperature below the boiling point of the chosen liquid aromatic hydrocarbon(s). Liquid clathrates that form at ambient temperatures (15 to 30° C.) are highly preferred. The pressure during clathrate formation is typically atmospheric. These clathrates are generally stable when heated, up to a deformation temperature, such temperature varying with the particular cation, anion, and solvent chosen.

The liquid clathrate is generally formed by mixing the liquid aromatic hydrocarbon with the tetrakis($^F$aryl)borate salt while agitating, until a readily recoverable liquid clathrate layer, immiscible with the liquid aromatic hydrocarbon, is formed. A two-layer mixture is usually formed, and the liquid clathrate is normally the lower layer. The layers are easily separable, for example by decantation. Once separated, the addition of excess nonsolvent, such as a nonaromatic hydrocarbon, or removal of the aromatic hydrocarbon comprising the liquid clathrate from the liquid clathrate layer by methods such as vacuum distillation, usually results in the isolation of the tetrakis($^F$aryl)borate salt as a solid. Because the liquid clathrate layer excludes other species, it is possible to obtain very pure tetrakis($^F$aryl) borate salts using liquid clathrate formation as a purification method.

The following examples are presented for purposes of illustration, and are not intended to impose limitations on the scope of this invention. In Examples 1, 2, and 4–7, bromomagnesium tetrakis(pentafluorophenyl)borate was obtained via a Grignard synthesis route.

EXAMPLE 1

Synthesis of $[(C_6H_5)(CH_3)_2NH][B(C_6F_5)_4]$ via Mg$[B(C_6F_5)_4]_2$ 20.0 g of a 20.77 wt% solution of $BrMgB(C_6F_5)_4$ (4.15 g, 5.3 mmol) in diethyl ether is added to 20.0 g of $H_2O$ at 25° C. during 15 minutes. The resultant two-layer mixture is stirred for one hour at 25° C. The lower liquid layer is then removed, yielding 16.4 g of ethereal solution. 2.91 mmol of Mg is present in the ethereal solution, as determined by ICP, and all of the $[B(C_6F_5)_4]^\ominus$ is in the ethereal solution, as determined by $^{19}$F NMR.

0.277 g (2.27 mmol) of $(C_6H_5)N(CH_3)_2$ and 0.554 g of 16 wt. % aqueous HCl (0.089 g, 2.43 mmol) are mixed, forming $[(C_6H_5)(CH_3)_2NH]Cl$. 0.554 g of $H_2O$ is added to the mixture. 5.0 g of the 22.3 wt% $Mg[B(C_6F_5)_4]_2$ (1.10 g, 0.80 mmol) solution in diethyl ether is added to the $[(C_6H_5)(CH_3)_2NH]Cl$ mixture with stirring. This mixture is stirred for two hours at 25° C. The ethereal and aqueous phases are then separated, the aqueous phase is washed with 2 g of diethyl ether, the two layers obtained are separated, and the ether washing is added to the original ethereal phase. The ethereal phase is then washed twice, each time with 1 g of $H_2O$. The yield of $[(C_6H_5)(CH_3)_2NH][B(C_6F_5)_4]$ is 86–89%, as determined by $^1$H and $^{19}$F NMR.

EXAMPLE 2

Synthesis of $[(C_6H_5)(CH_3)_2NH][B(C_6F_5)_4]$ via Mg$[B(C_6F_5)_4]_2$ 40.0 g of a 12.78 wt% solution of $BrMgB(C_6F_5)_4$ (5.11 g, 6.53 mmol) in diethyl ether is added to 40.0 g of HO at 25–-35° C. during 10 minutes. The resultant two-layer mixture is stirred for 30 minutes and then allowed to stand for 30 minutes. The lower liquid layer is then removed. The $Mg[B(C_6F_5)_4]_2$ is in the upper ethereal layer.

1.27 g (10.45 mmol) of $(C_6H_5)N(CH_3)_2$ and 2.68 g of 16 wt. % aqueous HCl (0.43 g, 11.75 mmol) are mixed, forming $[(C_6H_5)(CH_3)_2NH]Cl$. 3 g of $H_2O$ is added to the mixture. The $Mg[B(C_6F_5)_4]_2$ solution in diethyl ether is added to the $[(C_6H_5)(CH_3)_2NH]Cl$ mixture at 25° C. with stirring during 10 minutes. This mixture is stirred for two hours at 25° C., and then allowed to stand for 20 minutes. The ethereal and aqueous phases are then separated, and the ethereal phase is washed with two separate 6.0 g portions of $H_2O$, which are each separated from the ether layer. The diethyl ether is then removed at 22–30° C. under a partial vacuum, yielding 10.0 g of solid. 30.0 g of toluene are added to the solid; remaining ether and water, as well as some toluene, are removed at 75–80° C. under a partial vacuum. Another 30.0 g of toluene are added, and the mixture is again subjected to a partial vacuum at 75–80° C. to remove toluene. The resultant solids are dissolved by adding 30.0 g of $CH_2Cl_2$. 15.0 g of pentane are then added to the $CH_2Cl_2$ solution, precipitating $[(C_6H_5)(CH_3)_2NH][B(C_6F_5)_4]$. The solid was collected by filtration and washed with 15.0 of pentane. The solid is then dried at 25° C. in vacuo to yield 4.80 g of solid, an isolated yield of 91.95%. The purity of the $[(C_6H_5)(CH_3)_2NH][B(C_6F_5)_4]$ is 98%, as determined by $^1H$ and $^{19}F$ NMR.

EXAMPLE 3

Synthesis of $[(C_6H_5)_3C][B(C_6F_5)_4]$ from $Mg[B(C_6F_5)_4]_2$ 0.783 g of $Mg[B(C_6F_5)_4]_2$ (0.565 mmol) and 15.0 g of toluene are mixed at 25° C. 0.39 g of $(C_6H_5)_3CCl$ (1.4 mmol) is added to the $Mg[B(C_6F_5)_4]_2$/toluene mixture with stirring at 25° C. A red $[(C_6H_5)_3C][B(C_6F_5)_4]$/toluene liquid clathrate is observed. This mixture is stirred at 25° C. for twenty-four hours under nitrogen, forming a precipitate and two layers, consisting of an upper toluene layer and the red $[(C_6H_5)_3C][B(C_6F_5)_4]$/toluene liquid clathrate bottom layer, are formed. The mixture is filtered to remove the precipitate, which is washed with 5 g of toluene and then with 10 g of hexane. The upper layer is separated from the red clathrate layer, and 5 g of hexane are added to the separated red clathrate layer to precipitate the $[(C_6H_5)_3C][B(C_6F_5)_4]$. The solid $[(C_6H_5)_3C][B(C_6F_5)_4]$ is collected by filtration, washed with 5 g of hexane and dried, yielding 0.93 g of $[(C_6H_5)_3C][B(C_6F_5)_4]$, an isolated yield of 85%. 49 ppm of magnesium are present, as determined by ICP. The purity of the $[(C_6H_5)_3C][B(C_6F_5)_4]$ is 96.8–98.3%, as determined by $^1H$ and $^{19}F$ NMR.

EXAMPLE 4

Synthesis of $Na[B(C_6F_5)_4]$ via $Mg[B(C_6F_5)_4]_2$ 20.0 g of a 20.77 wt% solution of $BrMgB(C_6F_5)_4$ (4.15 g, 5.3 mmol) in diethyl ether is added to a mixture of 20.0 g of $H_2O$ and 20.0 g of diethyl ether at 25–35° C. with stirring during 30 minutes. The resultant two layers are separated, and the ethereal layer containing $Mg[B(C_6F_5)_4]_2$ is added to a solution of NaF (0.445 g, 10.6 mmol) in 20.0 g of $H_2O$ at 25° C. with stirring during 30 minutes. The resultant two-layer mixture is stirred for one hour at 25° C., and then allowed to stand for two hours. A rag is observed between the two layers. The lower aqueous layer is removed and washed with 20.0 g of diethyl ether; the resultant two layers are separated, and the upper ethereal wash layer is combined with the original ethereal layer. The combined ether solution is washed with 10.0 g of $H_2O$; the resultant two layers are separated, and the ether layer is added to boiling toluene (110° C.), and the ether and the water are distilled. The remaining liquid is cooled to 25° C. 40 g of pentane are added to precipitate the $Na[B(C_6F_5)_4]$. The liquids are decanted, and the solid $Na[B(C_6F_5)_4]$ is heated in vacuo at 25° C.; the yield of solid $Na[B(C_6F_5)_4]$ is 93.8%. The Na:Mg ratio in the solid is 70:1, as determined by ICP. The purity of the $Na[B(C_6F_5)_4]$ is 95.6% by ICP, and 96.0% by NMR. The $Na[B(C_6F_5)_4]$ contains traces of water and diethyl ether.

EXAMPLE 5

Synthesis of $K[B(C_6F_5)_4]$ via $Mg[B(C_6F_5)_4]_2$ 40.0 g of a 20.77 wt% solution of $BrMgB(C_6F_5)_4$ (8.30 g, 10.6 mmol) in diethyl ether is added to 40.0 g of $H_2O$ at 25–35° C. with stirring during 30 minutes. The resultant two layers are separated, and the ethereal layer containing $Mg[B(C_6F_5)_4]_2$ is washed with 40.0 g of $H_2O$. Because the phase boundary in the resultant two-layer mixture is unclear, a total of 40.0 g of diethyl ether are added to the mixture. The two layers are then separated, and the ether is removed from the ethereal layer, yielding an oil. 75 g of toluene is added to the oil and then distilled at 59° C. in a partial vacuum, yielding 8.19 g of solid $Mg[B(C_6F_5)_4]_2$, an isolated yield of 94.8%. The solid has a purity of 96.2%, and $^1H$ NMR indicates that the $Mg[B(C_6F_5)_4]_2$ may be a hydrate. The solid contains 4 mol % Br, as determined by XRF, and the Mg:B ratio is 1:2.07, as determined by ICP.

Solid $Mg[B(C_6F_5)_4]_2$ is added to a solution of $KHCO_3$ in $H_2O$ at 25° C. with stirring during 15 minutes. A white precipitate, $Mg(HCO_3)_2$, and two layers, consisting of an upper ethereal layer, which contains $K[B(C_6F_5)_4]$, and an aqueous bottom layer, are formed.

Repeating the above procedure using $NaHCO_3$ in place of $KHCO_3$ yielded analogous results.

EXAMPLE 6

Synthesis of $K[B(C_6F_5)_4]$ via $Mg[B(C_6F_5)_4]_2$ 40.0 g of a 20.77 wt% solution of $BrMgB(C_6F_5)_4$ (8.30 g, 10.6 mmol) in diethyl ether is added to 40.0 g of $H_2O$ at 25–35° C. with stirring during 30 minutes. The resultant two layers are separated, and the ethereal layer containing $Mg[B(C_6F_5)_4]_2$ is added to a solution of KF (1.80 g, 30.8 mmol) in 25 g of $H_2O$ at 25–30° C. with stirring during 30 minutes. The resultant two layers are separated, and the upper ethereal layer is washed with 5.0 g of $H_2O$. The resultant two layers are separated, and the ether is removed from the ethereal layer, which contains $K[B(C_6F_5)_4]$. 95 g of toluene are added to the solid $K[B(C_6F_5)_4]$, and the toluene is then distilled at 67–83° C. in a partial vacuum to remove residual water and diethyl ether. The solid obtained is washed with 30 g of toluene, and then with 40 g of pentane. The solid $K[B(C_6F_5)_4]$ is dried in vacuo at 25° C., yielding 6.9 g of $K[B(C_6F_5)_4]$ for an isolated yield of 90.7%. The K:Mg ratio in the solid is 265:1, as determined by ICP. The purity of the $K[B(C_6F_5)_4]$ is 98.5% as determined by ICP, and 97.3% as determined by NMR.

EXAMPLE 7

Synthesis of $K[B(C_6F_5)_4]$ via $Mg[B(C_6F_5)_4]_2$ 40.0 g of a 20.77 wt% solution of $BrMgB(C_6F_5)_4$ (8.30 g, 10.6 mmol) in diethyl ether is added to 40.0 g of $H_2O$ at 25–35° C. with stirring during 30 minutes. A two-phase mixture is obtained, and the lower aqueous layer is removed and washed with 20.0 g of diethyl ether. The ether washing is combined with the original ethereal layer, which contains $Mg[B(C_6F_5)_4]_2$, and the combined ether solution is added to a solution of $K_2CO_3$ (1.83 g, 13.3 mmol) in 20.0 g of $H_2O$ at 25–30° C. with stirring during 30 minutes. The resultant two layers are separated, and the upper ethereal layer is washed with 5.0 g of $H_2O$. Again, the resultant two layers are separated, and the ether is then removed from the separated ethereal layer, which contains $K[B(C_6F_5)_4]$. 93 g of toluene are added to the solid $K[B(C_6F_5)_4]$, and the toluene is then distilled at 77° C. in a partial vacuum. The solid $K[B(C_6F_5)_4]$ is dried in vacuo at 83° C. for one hour, yielding 7.6 g of $K[B(C_6F_5)_4]$ for a quantitative isolated yield. The purity of the $K[B(C_6F_5)_4]$ is 93%, as determined by NMR; it contains traces of fluorinated impurities, toluene, diethyl ether, and water.

EXAMPLE 8

Synthesis of $[(C_6H_5)_3C][B(C_6F_5)_4]$ from $K[B(C_6F_5)_4]$ 0.718 g of $K[B(C_6F_5)_4]$ (1 mmol) from Example 6 and 30 g of toluene are charged to a flask, and about two thirds of the toluene are distilled under nitrogen at 60–110° C. 0.363 g (1.3 mmol) of $(C_6H_5)_3CCl$ is added to the $K[B(C_6F_5)_4]$/toluene slurry during five minutes, forming a red-orange slurry. The mixture is stirred for twenty-four hours under nitrogen, forming a red $[(C_6H_5)_3C][B(C_6F_5)_4]$/toluene liquid clathrate bottom layer, a toluene upper layer, and a KCl precipitate. The mixture is filtered to collect the solid KCl; the KCl is washed with 3.0 g of toluene. The upper toluene layer is separated from the lower clathrate layer, and 20 g of hexane are added to the separated clathrate layer to precipitate the $[(C_6H_5)_3C][B(C_6F_5)_4]$. The solid $[(C_6H_5)_3C][B(C_6F_5)_4]$ is collected by filtration and washed with 4 g of hexane. The isolated yield of $[(C_6H_5)_3C][B(C_6F_5)_4]$ is 87% (the first crop of crystals). The purity of $[(C_6H_5)_3C][B(C_6F_5)_4]$ is 98.2%, as determined by $^{19}F$ NMR, a 96.9% as determined by $^1H$ NMR.

EXAMPLE 9

Synthesis of $[(n\text{-}octyl)_3NH][B(C_6F_5)_4]$ from $K[B(C_6F_5)_4]$ 6.3 g of diethyl ether and 0.71 g of $(n\text{-}octyl)_3N$ (2 mmol) are mixed. 1.61 g of ethereal HCl (1 molar, 2.2 mmol) is added to the mixture with stirring during ten minutes, forming $[(n\text{-}octyl)_3NH]Cl$. 1.48 g of $K[B(C_6F_5)_4]$ (2 mmol) are then added to the $[(n\text{-}octyl)_3NH]Cl$ mixture. The mixture is stirred at 25° C. for three hours, and then filtered to remove solid KCl. The ether is evaporated from the $[(n\text{-}octyl)_3NH][B(C_6F_5)_4]$, yielding an oil. 30 g of toluene are added to the oil at 25° C., forming a liquid clathrate; the toluene is then distilled at 50–80° C. in a partial vacuum, again yielding an oil. The oil is further dried in vacuo at 80° C., yielding a solid. The solid is washed with pentane, and the pentane is decanted. The solid is dried at 25° C., again in vacuo, yielding 1.5 g of $[(n\text{-}octyl)_3NH][B(C_6F_5)_4]$, an isolated yield of 75%. The purity of the ether-free $[(n\text{-}octyl)_3NH][B(C_6F_5)_4]$ is 98±2%, as determined by $^1H$ and $^{19}F$ NMR. One part of the ether-free $[(n\text{-}octyl)_3NH][B(C_6F_5)_4]$ is added to 8 parts (by weight) of toluene at 25° C.; a bottom oily layer is observed.

EXAMPLE 10

Synthesis of $Ph_2I[B(C_6F_5)_4]$ from $Na[B(C_6F_5)_4]$ 0.234 g of $Na[B(C_6F_5)_4]$ (0.33 mmol) from Example 4, further dried via a toluene azeotrope at 110° C., and 0.105 g of $Ph_2ICl$ (0.33 mmol) are stirred at 25–30° C. for 30 minutes. An orange bottom liquid clathrate layer and a clear upper layer are observed. NaCl precipitated, coating the wall of the reaction flask.

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. Whatever transformations, if any, that occur in situ as a reaction is conducted is what the claim is intended to cover. Thus the fact that a substance, component or ingredient may have lost its original identity through a chemical reaction or transformation during the course of contacting, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof.

Each and every patent or other publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A liquid clathrate that is formed from at least one liquid aromatic hydrocarbon and at least one tetrakis(aryl)borate salt, wherein each of the aryl groups is a fluorine-containing aryl group, each of which has bonded directly to an aromatic ring at least two fluorine atoms, or at least two perfluorohydrocarbyl groups, or at least one fluorine atom and at least one perfluorohydrocarbyl group, and wherein the cation is selected from a) a protic ammonium cation, wherein the protic ammonium cation has the formula $[R_3NH]^\oplus$, in which each R is independently a nonaryl hydrocarbyl group containing up to about thirty carbon atoms, b) an onium cation, wherein the onium cation has the formula $[ER_n]^\oplus$, wherein E is an element of any of Groups 15–17 of the Periodic Table, wherein each R is independently a hydrocarbyl group containing up to about thirty carbon atoms, and wherein n is equal to the valence of E plus one, and c) a triarylmethyl cation, wherein the triarylmethyl cation has three aryl groups bound to a central carbon atom, wherein the combination of said liquid aromatic hydrocarbon and said tetrakis(aryl)borate salt is effective to form a stable liquid clathrate.

2. A liquid clathrate according to claim 1 wherein the aromatic ring of said aryl group is a phenyl ring.

3. A liquid clathrate according to claim 1 wherein all of the positions on said aromatic ring(s) of said aryl group are substituted by fluorine atoms.

4. A liquid clathrate according to claim 3 wherein the tetrakis(aryl)borate is tetrakis(pentafluorophenyl)borate.

5. A liquid clathrate according to claim 1 wherein said cation of said at least one tetrakis(aryl)borate salt is a protic ammonium cation.

6. A liquid clathrate according to claim 5 wherein the protic ammonium cation is a tri(n-octyl)ammonium cation.

7. A liquid clathrate according to claim 1 wherein said cation of said at least one tetrakis(aryl)borate salt is an onium cation.

8. A liquid clathrate according to claim 7 wherein at least one R group of said onium cation is a phenyl group.

9. A liquid clathrate according to claim 7 wherein all of the R groups of said onium cation are the same.

10. A liquid clathrate according to claim 9 wherein said onium cation is a diphenyliodonium cation.

11. A liquid clathrate according to claim 1 wherein said at least one tetrakis(aryl)borate salt has a triarylmethyl cation.

12. A liquid clathrate according to claim 11 wherein said triarylmethyl cation is a triphenylmethyl cation.

13. A liquid clathrate according to claim 1 wherein the liquid aromatic hydrocarbon is toluene.

14. A liquid clathrate according to claim 1 wherein the weight ratio of tetrakis(aryl)borate salt to liquid aromatic hydrocarbon is at least about 1:1.

15. A liquid clathrate according to claim 1 wherein the liquid clathrate is formed at temperatures in the range of from about 15° C. to about 30° C.

* * * * *